United States Patent
Hahm et al.

(10) Patent No.: US 10,230,059 B2
(45) Date of Patent: Mar. 12, 2019

(54) ORGANIC COMPOUND AND ORGANIC THIN FILM AND ELECTRONIC DEVICE

(71) Applicant: Samsung Electronics Co., Ltd., Suwon-si, Gyeonggi-do (KR)

(72) Inventors: Suk Gyu Hahm, Gyungju-si (KR); Jeong Il Park, Seongnam-si (KR); Jiyoung Jung, Seoul (KR); Ajeong Choi, Suwon-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 115 days.

(21) Appl. No.: 15/168,968

(22) Filed: May 31, 2016

(65) Prior Publication Data

US 2016/0372686 A1    Dec. 22, 2016

(30) Foreign Application Priority Data

Jun. 19, 2015  (KR) .................. 10-2015-0087513
May 19, 2016  (KR) .................. 10-2016-0061613

(51) Int. Cl.
*H01L 51/00* (2006.01)
*H01L 51/05* (2006.01)
*C07D 495/22* (2006.01)
*C08G 75/00* (2006.01)

(52) U.S. Cl.
CPC ........ *H01L 51/0074* (2013.01); *C07D 495/22* (2013.01); *H01L 51/0071* (2013.01); *H01L 51/0072* (2013.01); *H01L 51/0073* (2013.01); *H01L 51/0558* (2013.01); *Y02E 10/549* (2013.01)

(58) Field of Classification Search
CPC ...... C08G 2261/3223; C08G 2261/126; C08G 2261/124; C08G 2261/95; C08G 2261/91; C07D 417/14; C07D 495/22; H01L 51/00; H01L 51/0074; H01L 51/0071; H01L 51/0072; H01L 51/0073; H01L 51/0558

See application file for complete search history.

(56) References Cited

U.S. PATENT DOCUMENTS

| | | | |
|---|---|---|---|
| 7,816,673 B2 | 10/2010 | Park et al. | |
| 2008/0142792 A1* | 6/2008 | Park et al. | C07D 495/22 257/40 |
| 2010/0065826 A1 | 3/2010 | Takimiya et al. | |
| 2010/0305288 A1* | 12/2010 | He | C07D 495/22 526/256 |
| 2013/0116447 A1 | 5/2013 | Park et al. | |
| 2013/0320316 A1* | 12/2013 | Park | H01L 51/05 257/40 |
| 2015/0218185 A1 | 8/2015 | Takimiya et al. | |
| 2015/0239901 A1 | 8/2015 | Takimiya et al. | |

FOREIGN PATENT DOCUMENTS

| | | | | |
|---|---|---|---|---|
| JP | 2010-177642 A | 8/2010 | | |
| JP | 2010-177643 A | 8/2010 | | |
| JP | 2010177643 | * 8/2010 | ............. H01L 51/30 |

(Continued)

*Primary Examiner* — Shane Fang

(74) *Attorney, Agent, or Firm* — Harness, Dickey & Pierce, P.L.C.

(57) ABSTRACT

An organic compound is represented by Chemical Formula 1, and an organic thin film, a thin film transistor, and an electronic device includes the organic compound.

13 Claims, 5 Drawing Sheets

(56) References Cited

FOREIGN PATENT DOCUMENTS

| KR | 2013-0050266 A | 5/2013 |
|----|----------------|--------|
| WO | WO-2008/050726 A1 | 5/2008 |
| WO | WO-2009/009790 A1 | 1/2009 |
| WO | WO-2014/027581 A1 | 2/2014 |
| WO | WO-2014/030700 A1 | 2/2014 |

* cited by examiner

ORGANIC COMPOUND AND ORGANIC THIN FILM AND ELECTRONIC DEVICE

CROSS REFERENCE TO RELATED APPLICATIONS

This application claims priority to and the benefits of Korean Patent Application No. 10-2015-0087513 filed in the Korean Intellectual Property Office on Jun. 19, 2015, and Korean Patent Application No. 10-2016-0061613 filed in the Korean Intellectual Property Office on May 19, 2016, the entire contents of each of which are incorporated herein by reference.

BACKGROUND

1. Field

Example embodiments relate to an organic compound, an organic thin film, and an electronic device.

2. Description of the Related Art

A flat panel display (e.g., a liquid crystal display (LCD), an organic light emitting diode (OLED) display, and/or an electrophoretic display) includes a pair of electric field-generating electrodes and an electrical optical active layer interposed therebetween. The liquid crystal display (LCD) includes a liquid crystal layer as an electric optical active layer, and the organic light emitting diode (OLED) display includes an organic emission layer as an electrical optical active layer.

One of the pairs of the electric field-generating electrodes is commonly connected to a switching device and receives an electrical signal, and the electrical optical active layer transforms the electrical signal into an optical signal and thus displays an image.

A flat panel display includes a thin film transistor (TFT) that is a three-terminal element as a switch, a gate line that transmits a scan signal to control the thin film transistor, and a data line that transmits a signal applied to a pixel electrode.

Research on an organic thin film transistor (OTFT) including an organic semiconductor, e.g., a relatively low molecular weight semiconductor, or polymer semiconductor instead of an inorganic semiconductor, e.g., a silicon (Si) semiconductor, as one type of thin film transistor is being actively conducted.

The organic thin film transistor may be made into a fiber or a film due to characteristics of an organic material, and thus is drawing attention as a core element for a flexible display device. The organic thin film transistor may be made by a solution process, e.g., inkjet printing, and thus, may be more easily applied to relatively large area flat panel display devices limited only by a deposition process.

SUMMARY

Example embodiments provide an organic compound that is applicable to an electronic device, e.g., an organic thin film transistor.

Example embodiments also provide an organic thin film including the organic compound.

Example embodiments also provide an electronic device including the organic compound.

According to example embodiments, an organic compound is represented by Chemical Formula 1.

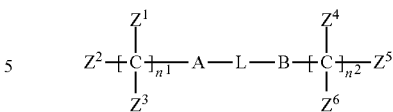

[Chemical Formula 1]

In Chemical Formula 1, each of A and B are independently one of a substituted or unsubstituted $C_6$ to $C_{30}$ arylene group, a divalent substituted or unsubstituted $C_2$ to $C_{30}$ heterocyclic group, and a combination thereof, each of $Z^1$ to $Z^6$ are independently one of hydrogen, a $C_1$ to $C_{10}$ haloalkyl group, and a halogen, provided that at least one of $Z^1$ to $Z^6$ is one of a $C_1$ to $C_{10}$ haloalkyl group and a halogen, each of $n^1$ and $n^2$ are independently an integer of 0 to 5, and L is a condensed polycyclic group including 6 or more fused rings and a group represented by Chemical Formula 2,

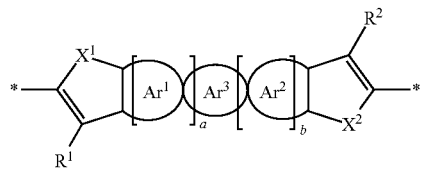

[Chemical Formula 2]

wherein, in Chemical Formula 2, each of $Ar^1$ and $Ar^2$ are independently one of a substituted or unsubstituted five-membered ring and a substituted or unsubstituted six-membered ring, $Ar^3$ is one of

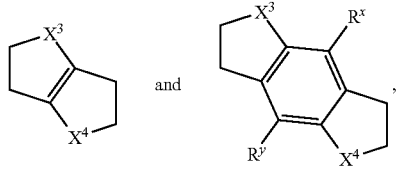

each of $X^1$ to $X^4$ are independently one of O, S, Se, Te, and $NR^a$, each of $R^1$, $R^2$, $R^a$, $R^x$, and $R^y$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof, each of a and b are independently an integer ranging from 1 to 3, and

* is a linking point, when in Chemical Formula 2, $Ar^3$ is

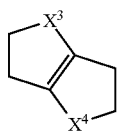

and a=b=1, the L is a group represented by Chemical Formula 3:

[Chemical Formula 3]

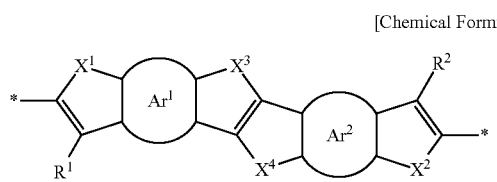

wherein, in Chemical Formula 3, $Ar^1$, $Ar^2$, $X^1$ to $X^4$, $R^1$, $R^2$ and * are the same as defined in Chemical Formula 2.

Each of the $Ar^1$ and $Ar^2$ may independently be one of a substituted or unsubstituted benzene ring and a substituted or unsubstituted heterocyclic group.

Each of the $Ar^1$ and $Ar^2$ may be a substituted or unsubstituted benzene ring.

In Chemical Formula 2, a and be may satisfy a=b=1 or a=b=2.

The L may be represented by one of the following compounds of Group 1.

[Group 1]

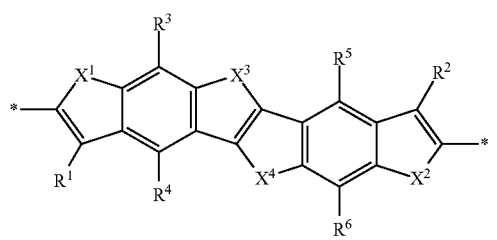

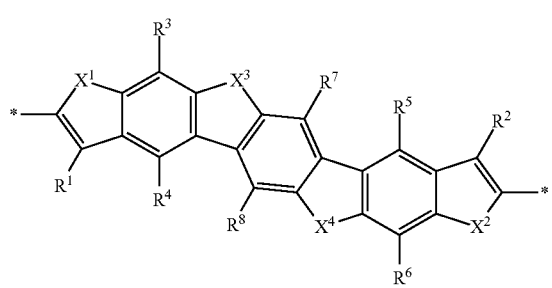

-continued

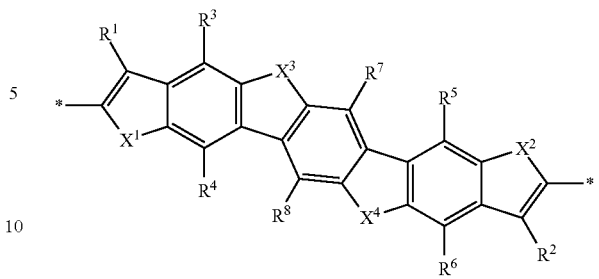

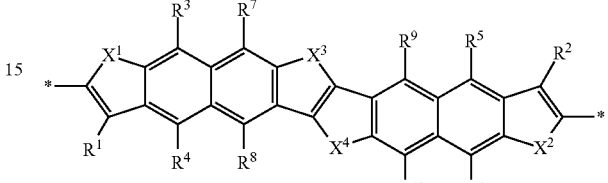

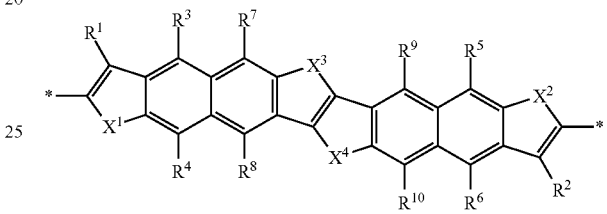

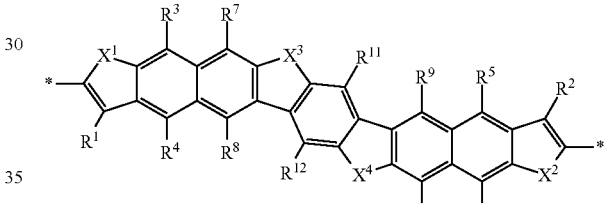

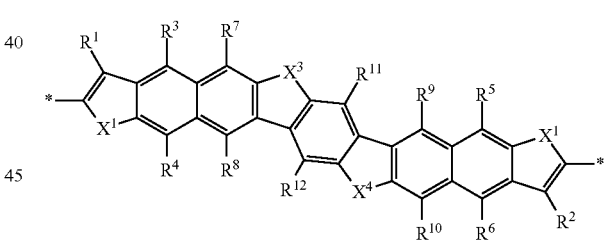

In Group 1, each of $X^1$ to $X^4$ are independently one of O, S, Se, Te, and $NR^a$, each of $R^1$ to $R^{12}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ alkynyl group, a hydroxy group, a halogen, and a combination thereof, and

* is a linking point.

Each of the A and B may independently be represented by one of the following compounds of Group 2.

[Group 2]

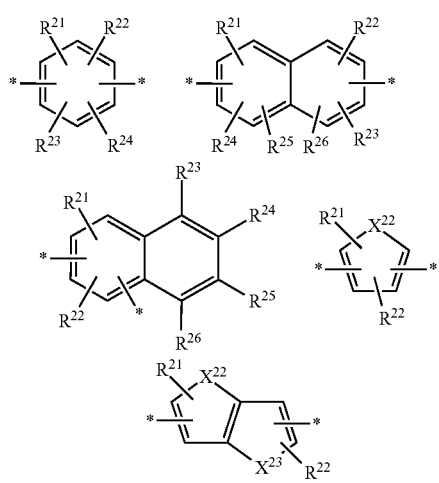

In Group 2, each of $X^{21}$ to $X^{23}$ are independently one of O, S, Se, Te, and $NR^a$, each of $R^{21}$ to $R^{26}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof, and

* is a linking point.

Each of the $Z^1$ to $Z^6$ may independently be a halogen.

The organic compound may be is represented by one of the following compounds of Group 3.

[Group 3]

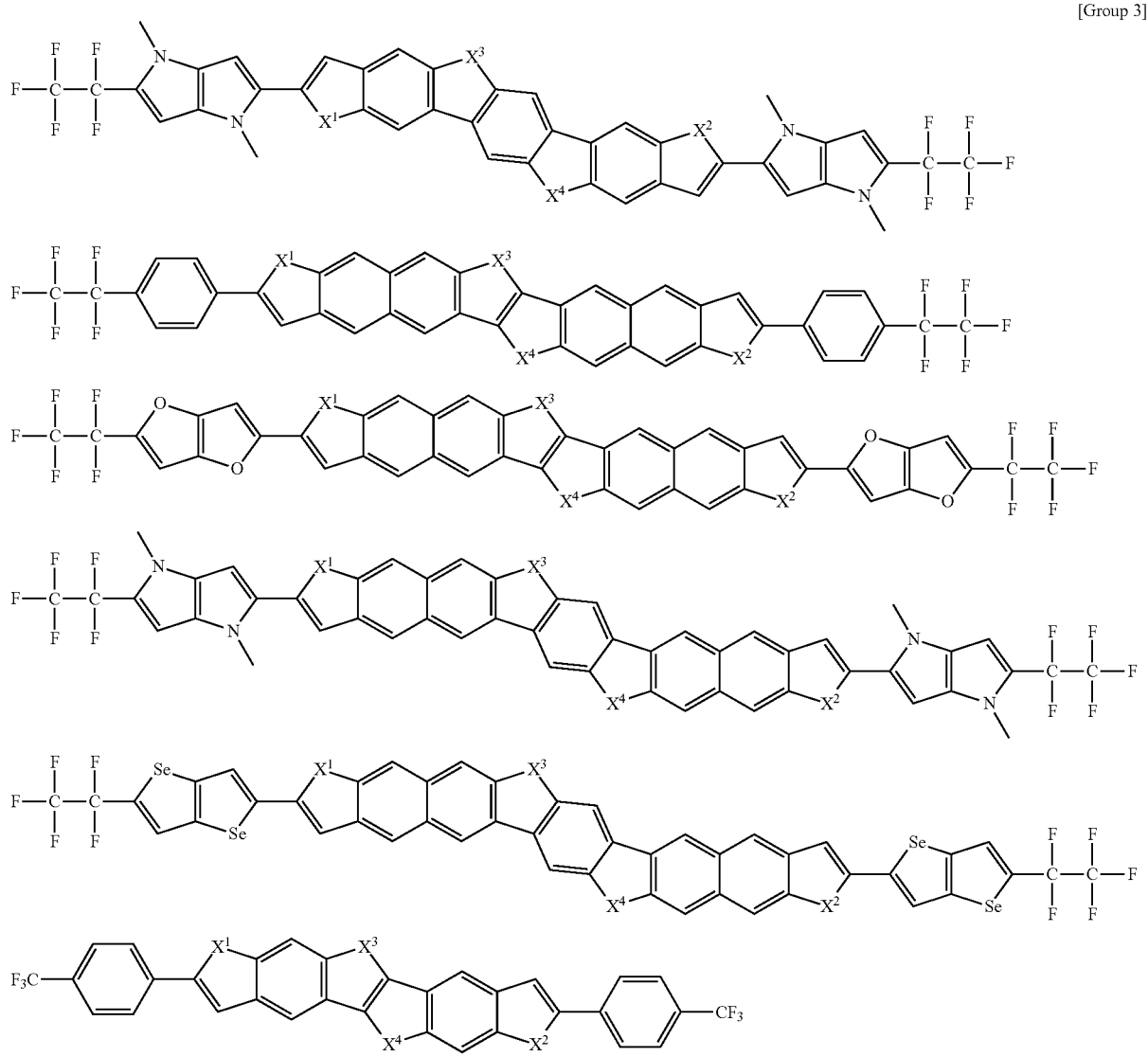

-continued

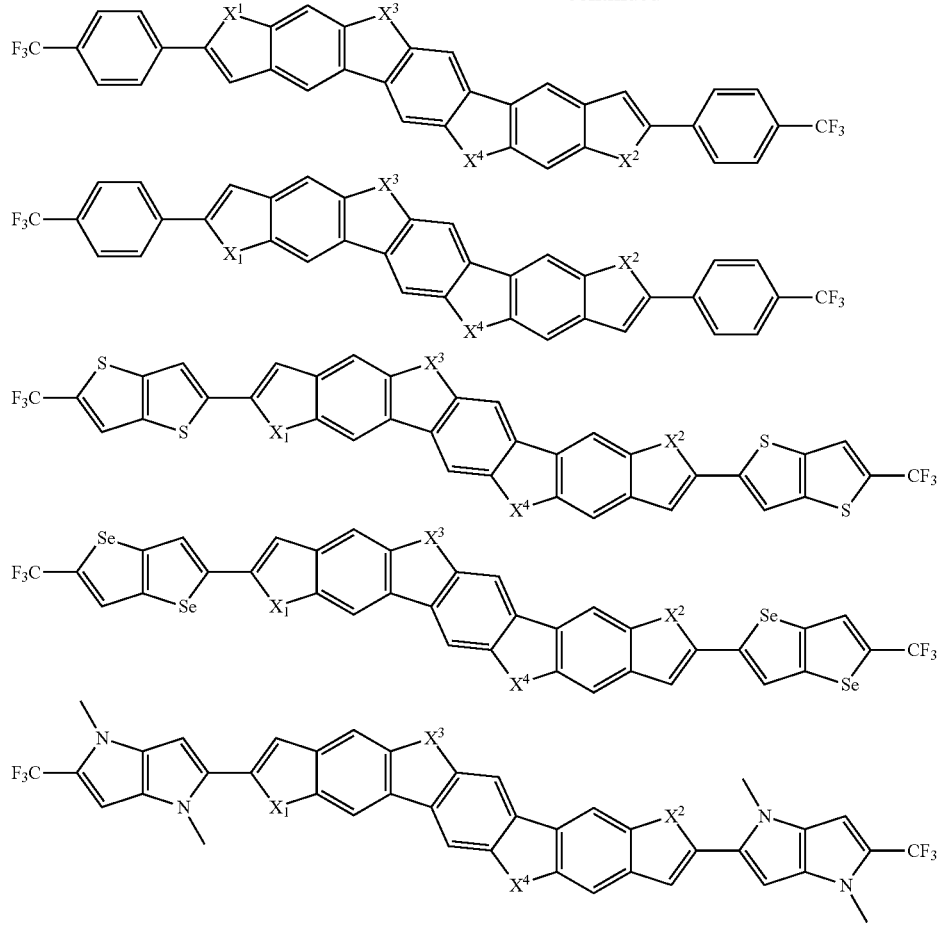

In Group 3, each of $X^1$ to $X^4$ are independently one of O, S, Se, Te, and $NR^a$, $R^a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof.

According to example embodiments, an organic thin film includes the organic compound.

According to example embodiments, an electronic device includes the organic compound.

According to example embodiments, a thin film transistor includes a gate electrode, an organic semiconductor overlapping the gate electrode, and a source electrode and a drain electrode electrically connected to the organic semiconductor, wherein the organic semiconductor includes an organic compound represented by Chemical Formula 1.

According to example embodiments, an electronic device includes the thin film transistor.

The electronic device may include one of a solar cell, a liquid crystal display, an organic light emitting device, an electrophoretic device, an organic photoelectric device, and an organic sensor.

DETAILED DESCRIPTION

Figure 1:
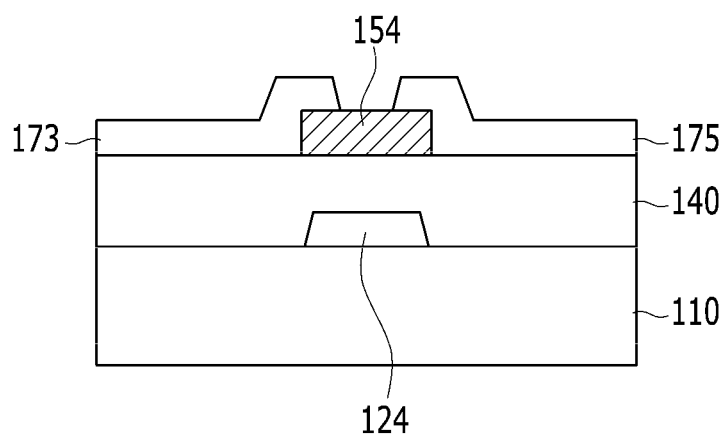
FIG. 1 is a cross-sectional view showing a thin film transistor according to example embodiments.

Example embodiments will hereinafter be described in detail, and may be easily performed by those who have common knowledge in the related art. However, this disclosure may be embodied in many different forms and is not construed as limited to the example embodiments set forth herein.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term 'substituted' refers to substitution with a halogen (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_{30}$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, $C_3$ to $C_{30}$ heterocycloalkyl group, and a combination thereof, instead of hydrogen of a compound.

As used herein, when a definition is not otherwise provided, the term 'hetero' refers to one including 1 to 3 hetero atoms selected from N, O, S, Se, and P.

Hereinafter, an organic compound according to example embodiments is described.

An organic compound according to example embodiments is represented by Chemical Formula 1.

[Chemical Formula 1]

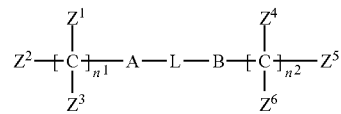

In Chemical Formula 1, each of A and B are independently one of a substituted or unsubstituted $C_6$ to $C_{30}$ arylene group, a divalent substituted or unsubstituted $C_2$ to $C_{30}$ heterocyclic group, and a combination thereof, each of $Z^1$ to $Z^6$ are independently one of hydrogen, a $C_1$ to $C_{10}$ haloalkyl group, and a halogen, provided that at least one of $Z^1$ to $Z^6$ is one of a $C_1$ to $C_{10}$ haloalkyl group and a halogen, each of $n^1$ and $n^2$ are independently an integer of 0 to 5, and L is a condensed polycyclic group including a fused ring of six or more rings and a group represented by Chemical Formula 2,

[Chemical Formula 2]

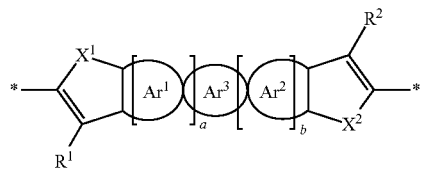

wherein, in Chemical Formula 2, each of $Ar^1$ and $Ar^2$ are independently one of a substituted or unsubstituted five-membered ring and a substituted or unsubstituted six-membered ring, $Ar^3$ is one of

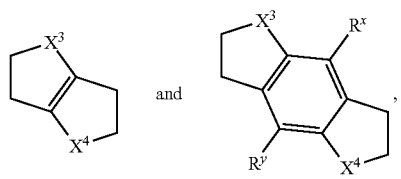

each of $X^1$ to $X^4$ are independently one of O, S, Se, Te, and $NR^a$, each of $R^1$, $R^2$, $R^a$, $R^x$, and $R^y$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof, each of a and b are independently an integer ranging from 1 to 3, and \* is a linking point, when in Chemical Formula 2, $Ar^3$ is

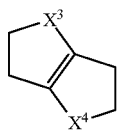

and a=b=1, the L is a group represented by Chemical Formula 3:

[Chemical Formula 3]

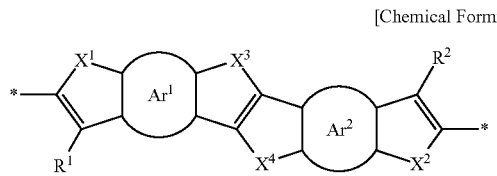

wherein, in Chemical Formula 3, $Ar^1$, $Ar^2$, $X^1$ to $X^4$, $R^1$, $R^2$ and \* are the same as defined in Chemical Formula 2.

The organic compound is a low molecular weight compound in which L, a condensed polycyclic group including a fused ring of six or more rings, is placed in the core moiety, and halogen is contained at the terminal end, and the core moiety and the terminal end are connected by a predetermined cyclic group. The organic compound may increases the planarity thereof by appropriately adjusting the number of fused rings at the core moiety, so that the packing and stacking between molecules may be increased. In addition, the organic compound contains halogen at the terminal end, so the interaction between thermal ends is enhanced by Van der Waals forces between halogens, and also the pi-pi interaction between core moieties is enhanced, so as to further improve an intermolecular interaction or an intermolecular space structure.

Each of the $Ar^1$ and $Ar^2$ may independently be one of a substituted or unsubstituted benzene ring and a substituted or unsubstituted heterocyclic group.

For example, the L is a fused ring of a substituted or unsubstituted benzene ring and a substituted or unsubstituted heterocyclic group, and for example the $Ar^1$ and $Ar^2$ may be a substituted or unsubstituted benzene ring.

For example, when the $Ar^1$ or $Ar^2$ is a substituted or unsubstituted heterocyclic group, $Ar^1$ or $Ar^2$ may be a heterocyclic group including O, S, Se, Te, or $NR^a$, wherein the $R^a$ is hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, or a combination thereof.

For example, the condensed polycyclic group represented by L may have a symmetric structure, for example a and b may simultaneously be 1 or a and b may simultaneously be 2, but is not limited thereto.

The L may be represented by one of the following compounds of Group 1, but is not limited thereto.

[Group 1]

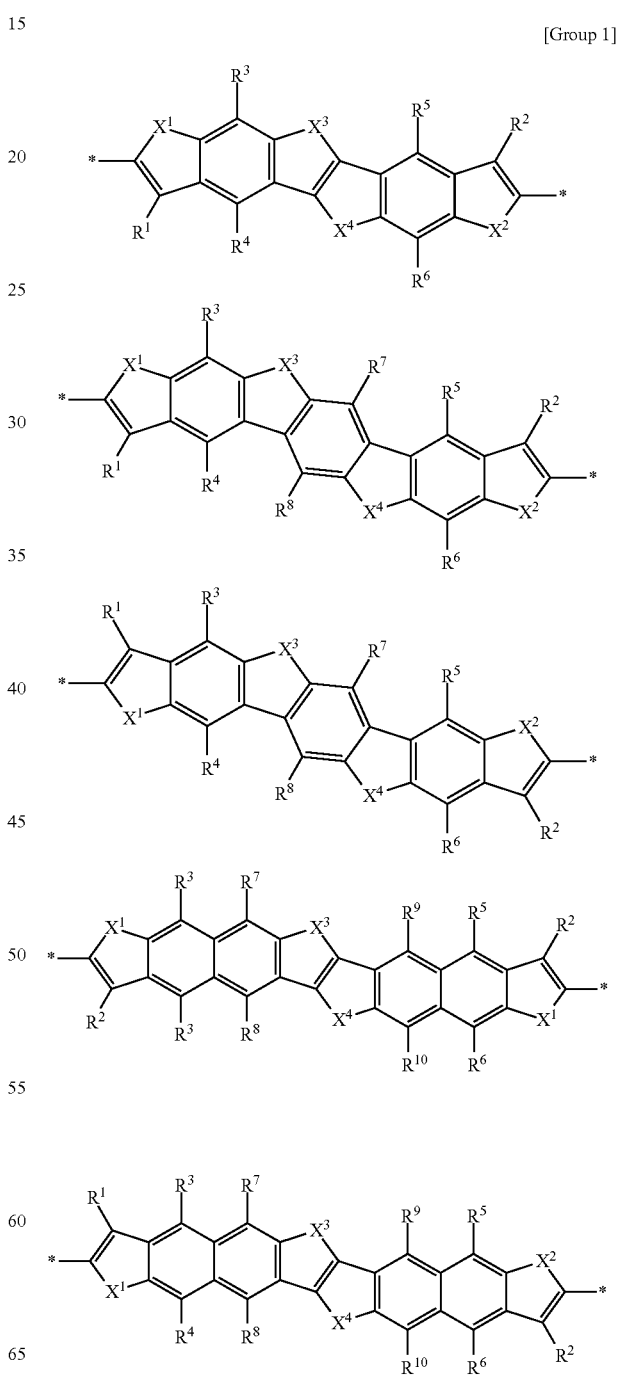

-continued

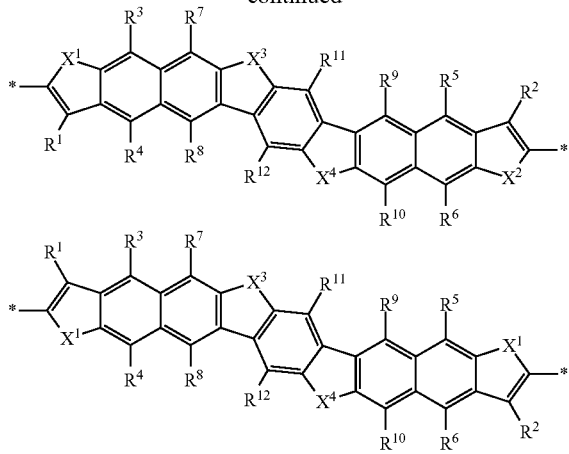

In Group 1,
each of $X^1$ to $X^4$ are independently one of O, S, Se, Te, and $NR^a$, each of $R^1$ to $R^{12}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ alkynyl group, a hydroxy group, a halogen, and a combination thereof, and

* is a linking point.

As described above, the organic compound contains at least one halogen at the terminal end, and the at least one halogen may be contained in one side terminal end or may be contained in both terminal ends. For example, the halogen may be fluorine. For example, in Chemical Formula 1, each of $Z^1$ to $Z^6$ may independently be a halogen (e.g., fluorine (F), chlorine (Cl), bromine (Br), or iodine (I)). For example, all $Z^1$ to $Z^6$ may be fluorine. For example, in Chemical Formula 1, each of $n^1$ and $n^2$ may independently be an integer of 1 to 5, for example 1 or 2, but is not limited thereto.

In Chemical Formula 1, A and B may be, for example one of substituted or unsubstituted groups of Group 2, but is not limited thereto.

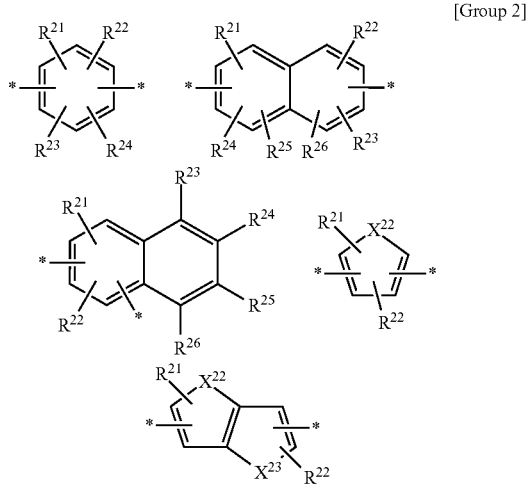

In Group 2,
each of $X^{21}$ to $X^{23}$ are independently one of O, S, Se, Te, and $NR^a$, each of $R^{21}$ to $R^{26}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof, and

* is a linking point.

The organic compound may be, for example, represented by one of the following compounds of Group 3, but is not limited thereto.

[Group 3]

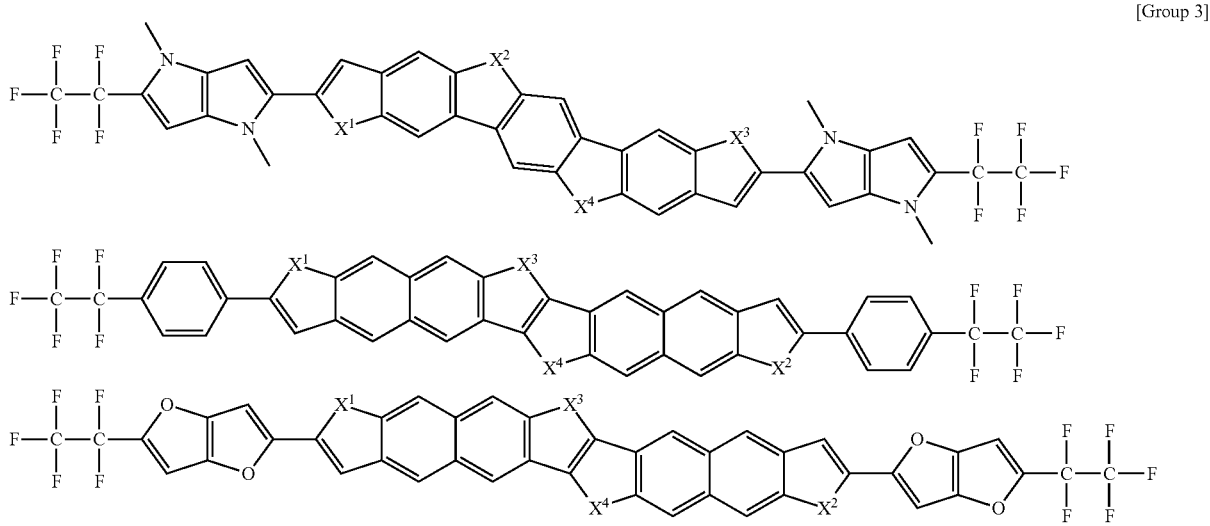

-continued

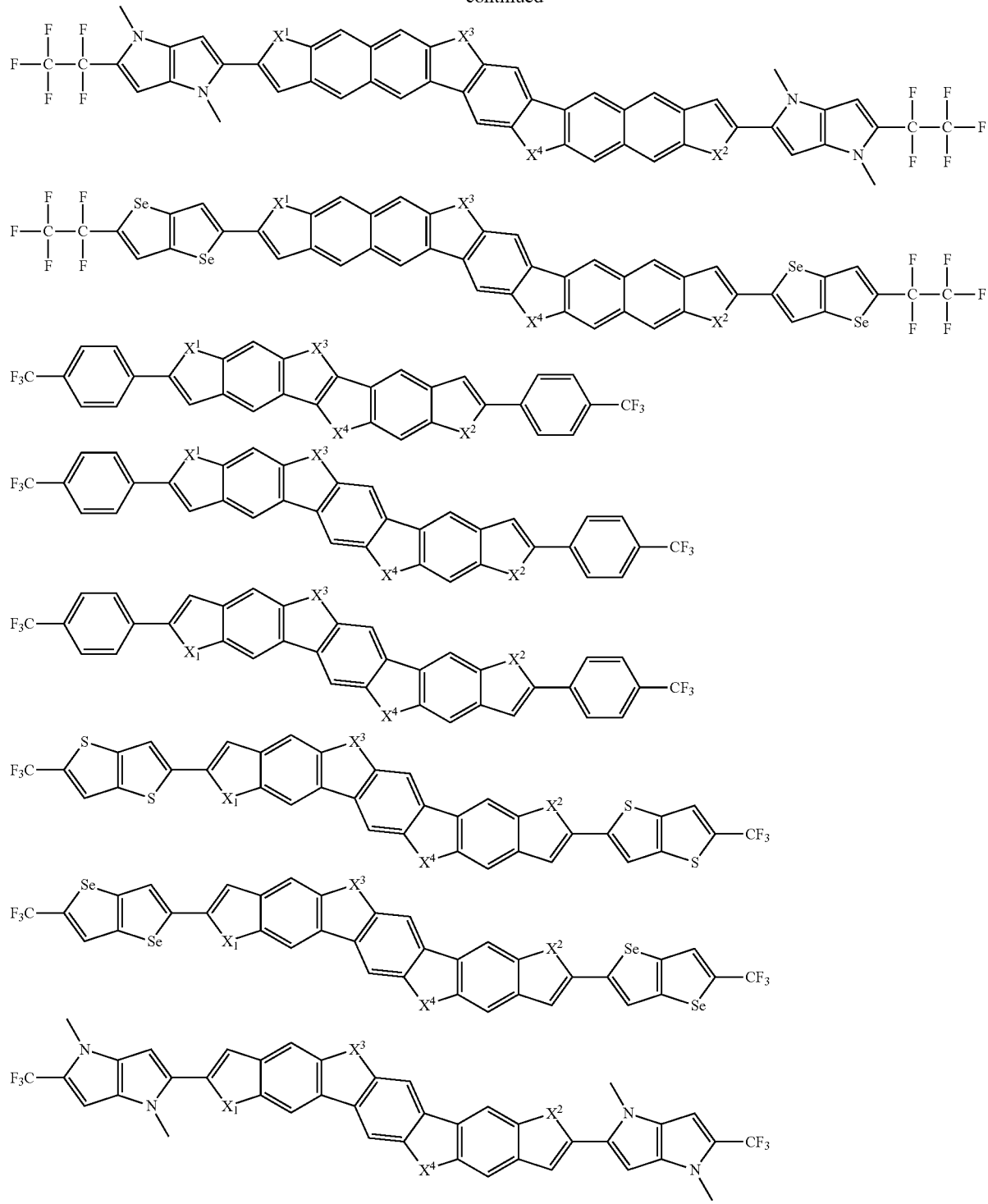

In Group 3,
each of $X^1$ to $X^4$ are independently one of O, S, Se, Te, and $NR^a$,
$R^a$ is independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof.

The organic compound may be used for making an organic thin film by a deposition or solution processes. The organic thin film may be applied to various devices including an organic semiconductor. For example, the organic compound may be applied to a thin film transistor, and may be applied as a charge transport layer and/or active layer in an electronic device, e.g., a solar cell, a liquid crystal display (LCD), organic light emitting display device, an electrophoretic device, an organic photoelectric device, and an organic sensor.

Hereinafter, one example of a thin film transistor including the organic compound is illustrated referring to drawings.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

FIG. 1 is a cross-sectional view showing a thin film transistor according to example embodiments.

A gate electrode 124 is formed on a substrate 110 made of a transparent glass, silicon, or plastic. The gate electrode 124 is connected to a gate line (not shown) transmitting a data signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material, examples of the organic material may include a polyvinyl alcohol-based compound, a polyimide-based compound, a polyacryl-based compound, a polystyrene-based compound, and a dissoluble polymer compound (e.g., benzocyclobutane (BCB), and examples of the inorganic material may include a silicon nitride ($SiN_x$) and a silicon oxide ($SiO_2$)).

A source electrode 173 and a drain electrode 175 are formed on the gate insulating layer 140. The source electrode 173 and the drain electrode 175 face each other in the center of the gate electrode 124. The source electrode 173 is electrically connected to is connected to a data line (not shown) transmitting a data signal. The source electrode 173 and drain electrode 175 may be made of, for example, gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the organic compound.

The organic semiconductor 154 may be formed by preparing the organic compound in a form of a solution and a solution process, for example spin coating, slit coating or inkjet printing. However, the organic semiconductor 154 may be formed by a dry process, e.g., deposition of the organic compound.

Herein, as one example of a thin film transistor, a thin film transistor having a bottom gate structure is illustrated, but is not limited thereto, and may be applied to a thin film transistor having a top gate structure in the same manner.

The thin film transistor may be applied as a switch or driving device of various electronic devices, and the electronic device may include, for example a liquid crystal display (LCD), an organic light emitting display device, an electrophoretic display device, an organic photoelectric device, and an organic sensor.

Hereinafter, the present disclosure is illustrated in more detail with reference to examples. However, these are examples, and the present disclosure is not limited thereto.

SYNTHESIS OF ORGANIC COMPOUNDS

Synthesis Example 1

(Synthesis of Compound P1)

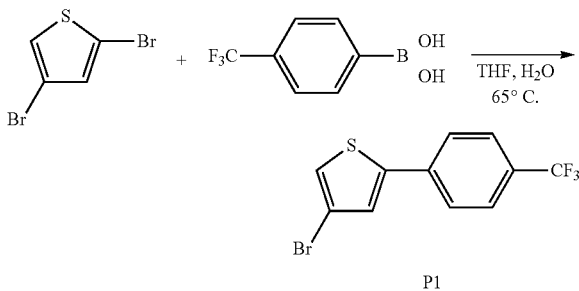

8 g (33 mmol) of 2,4-dibrom thiophene, 7.52 g (39.6 mmol) of 4-(trifluoromethyl)boronic acid, 8.66 g (66 mmol) of potassium carbonate, 0.953 g (0.825 mmol) of tetrakis (triphenylphosphine)palladium (0), 640 ml of THF, and 40 ml of water are placed in 2000 ml two-neck flask and refluxed at 65° C. for 12 hours. Then the reaction is completed by water and chloroform and worked-up. Subsequently, it is purified by hexane using a column chromatography to provide Compound P1. (yield: 71%)

(Synthesis of Compound P2)

0.515 g (1.68 mmol) of Compound P1 is placed in a 100 ml one-neck flask and dissolved in 20 ml of THF. After the temperature is dropped to −78° C., 0.84 ml (1.68 mmol) of LDA is added thereto. Then 0.15 g (0.765 mmol) of thieno[3,2-b]thiophene-2,5-dicarbaldehyde is added thereto. After 12 hours, the reaction is completed by sodium hydrogen carbonate and worked-up with chloroform. Subsequently, it is recrystallized using chloroform to provide Compound P2. (yield: 46%)

(Synthesis of Compound P3)

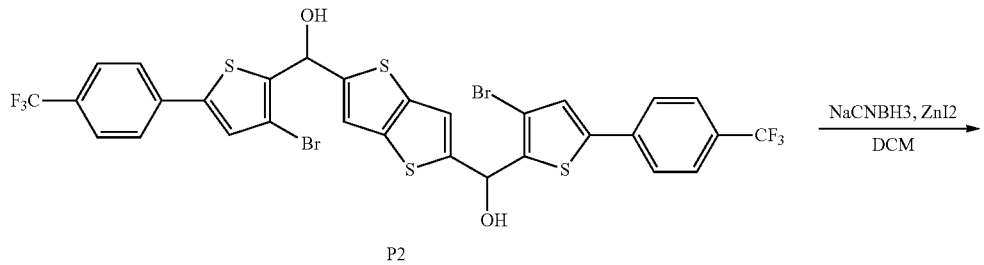

P2

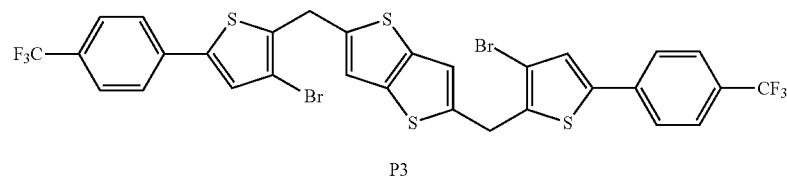

P3

0.38 g (0.468 mmol) of Compound P2, 0.44 g (3.52 mmol) of sodium cyanoborohydride (NaCNBH$_3$) and zinc iodide (ZnI$_2$) are placed in 250 ml 2-neck flask. 70 ml of 1,2 dichloroethane is added thereto and refluxed at a temperature of 40° C. and left to stand overnight. 50 ml of water is slowly poured into a reaction vessel and slowly added with 1N HCl to complete the reaction. After the work-up by chloroform, it is purified by precipitation using methanol to provide Compound P3 (yield: 80%).

(Synthesis of Compound P4)

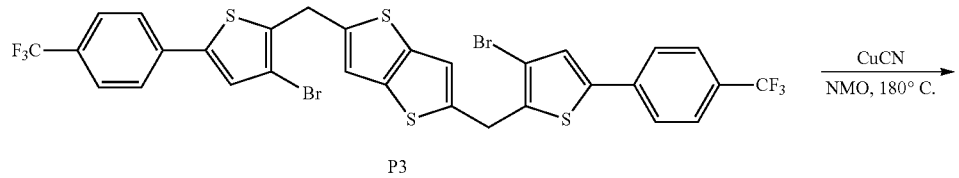

P3

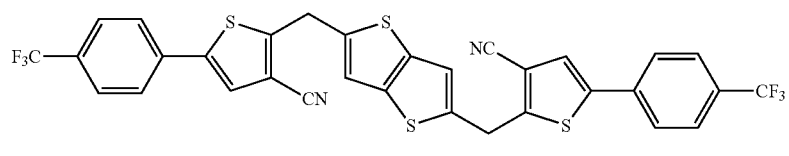

P4

1.0 g of Compound P3, 0.6 g of CuCN and 20 ml of NMP are placed in 50 ml vial and reacted in a microwave reactor at a temperature of 180° C. for 1 hour and 30 minutes. Then the reaction is completed by 1 N HCl solution and worked-up using DCM. Then it is purified by precipitation using ethyl acetate to provide Compound P4 (yield: 85%).

(Synthesis of Compound P5)

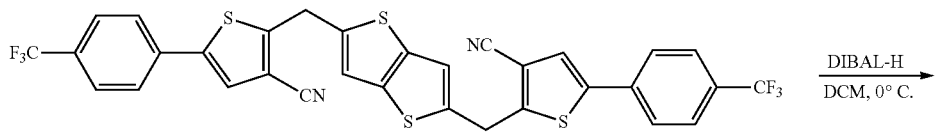

P4

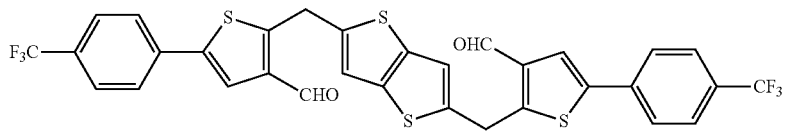

P5

1.82 g (2.72 mmol) of Compound P4 is dissolved in 200 ml of DCM and cooled down to a temperature of −10° C. Then 8.5 ml (8.16 mmol) of DIBAL-H is slowly added thereto. After 2 hours at −10° C., 1N HCl (MeOH (3): H₂O (1)) is slowly added thereto. Then the temperature is slowly increased up to a room temperature. Then an organic layer is isolated using water and DCM. It is separated and purified by a column chromatography using chloroform to provide Compound P5. (yield: 39%)

(Synthesis of Compound P6)

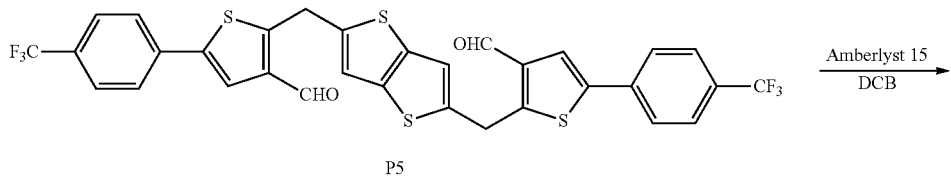

P5

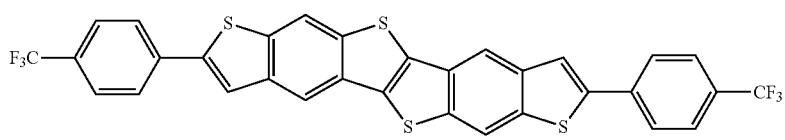

P6

1.0 g of compound P5, 1.0 g of Amberlyst 15 (manufactured by Sigma-Aldrich), and 20 ml of 1,2-Dichorobenzene are added and reacted in a microwave reactor at 120° C. for 14 hours. After the temperature is dropped to a room temperature, it is separated and purified by decanting the same using ethyl acetate to provide Compound P6. (yield: 50%)

Subsequently, the real structure of the final compound (Compound P6) obtained from Synthesis Example 1 is confirmed by a MALDI-TOF mass analysis.

Figure 2:
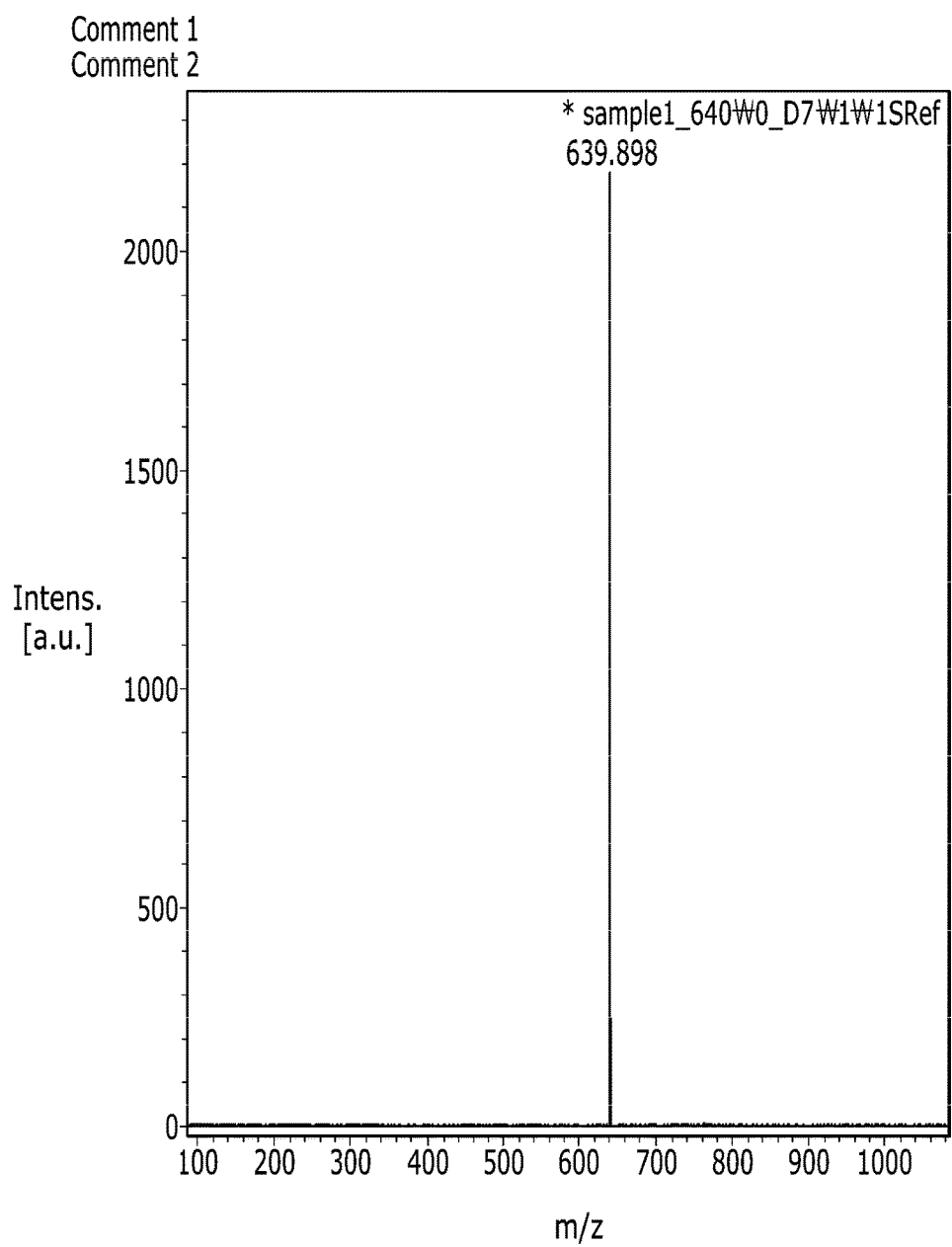
FIG. 2 shows an MALDI-TOF mass analysis data of the compound according to Synthesis Example 1.

FIG. 2 shows an MALDI-TOF mass analysis data of the final compound according to Synthesis Example 1 (m/z=639.898). Referring to FIG. 2, the compound of Synthesis Example is actually obtained.

Synthesis Example 2

(Synthesis of Compound P2')

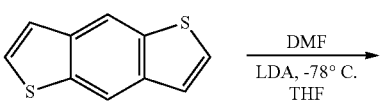

-continued

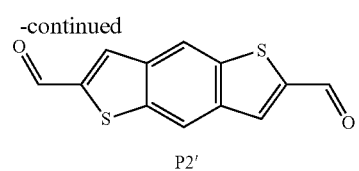

P2'

0.5 g (2.63 mmol) of benzo[1,2-b:4,5-b']dithiophene is dissolved in 30 ml of THF, and after cooling the temperature up to −78° C. under the nitrogen atmosphere, a lithium diisopropylamine (LDA) solution (2.0 M, 3.0 ml, 5.8 mmol, 2.2 equiv.) is carefully added thereto. Then when reaching to 0° C., the temperature is dropped again to −78° C., and anhydrous dimethylformamide (0.6 ml, excess) is added thereto. When reaching the room temperature, 1N HCl solution is added thereto and stirred for 20 minutes. Then pH is neutralized by adding NaHCO₃ having a 1N concentration. Then the organic layer is extracted by dichloromethane, and moisture is removed using MgSO₄ and dried. Then it is purified using column chromatography to provide Compound P2' (yield: 80%).

(Synthesis of Compound P3')

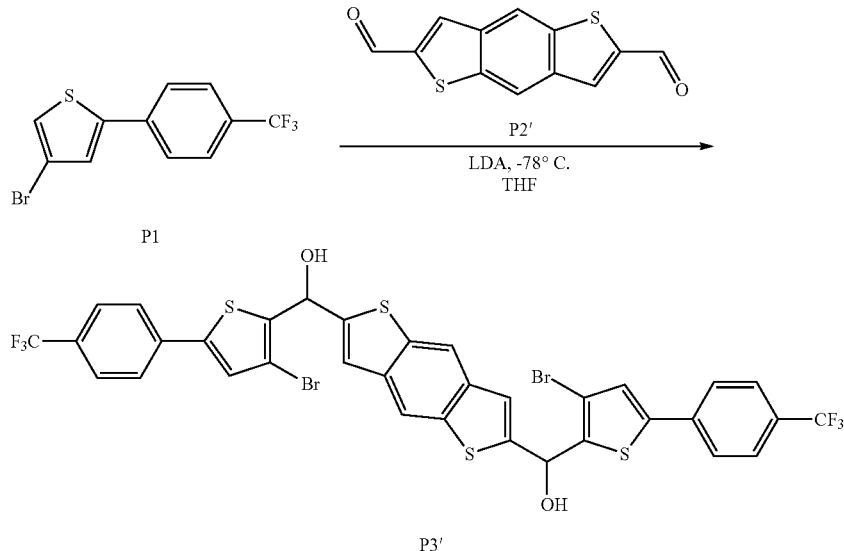

1.35 g (4.4 mmol) of Compound P1 obtained from Synthesis Example 1 is placed in 100 ml one-neck flask and dissolved in 30 ml of THF. Then after the temperature is dropped to −78° C., 2.2 ml (4.4 mmol) of LDA is added thereto. Then 0.5 g (2.0 mmol) of benzo[1,2-b:4,5-b']dithiophene-dicarbaldehyde is added thereto. After 12 hours, the reaction is completed by sodium hydrogen carbonate and worked-up by chloroform. Then it is recrystallized by chloroform to provide Compound P3' (yield: 65%).

(Synthesis of Compound P4')

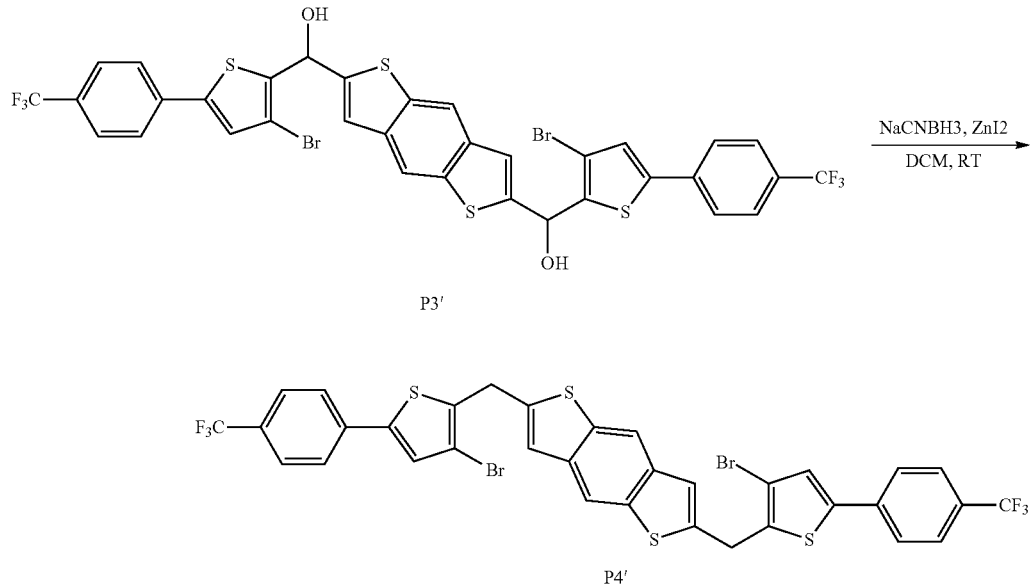

3.8 g (4.42 mmol) of P3', 4.44 g (70.72 mmol) of sodium cyanoborohydride (NaCNBH$_3$), and 5.64 g (17.68 mmol) of zinc iodide (ZnI$_2$) are placed in 1000 ml two-neck flask. 600 ml of 1,2 dichloroethane is added thereto and refluxed at a temperature of 40° C. and left to stand overnight. 50 ml of water is slowly poured to the reaction vessel, and then 1N HCl is slowly added to complete the reaction. After the work-up by chloroform, it is purified by precipitation using methanol to provide Compound P4' (yield: 80%).

(Synthesis of Compound P5')

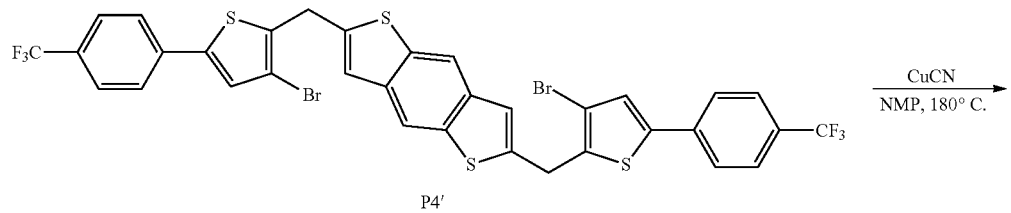

P4'

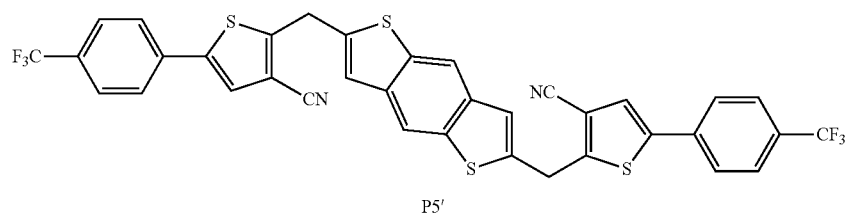

P5'

1.0 g of P4' and 0.45 g of CuCN, 20 ml of NMP are placed into 50 ml vial and reacted in a microwave reactor at a temperature of 180° C. for 1 hour 30 minutes. Then the reaction is completed by 1 N HCl solution and worked-up using DCM. Then the precipitation is separated using ethyl acetate to provide Compound P5' (yield: 60%).

(Synthesis of Compound P6')

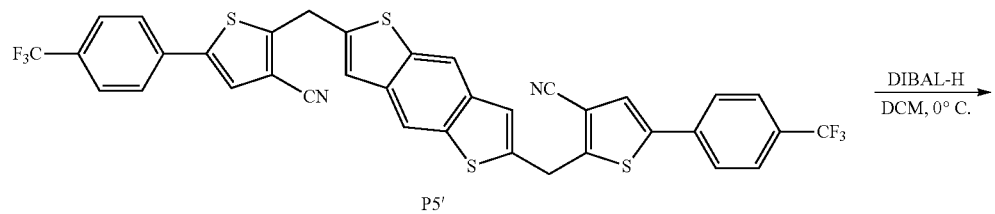

P5'

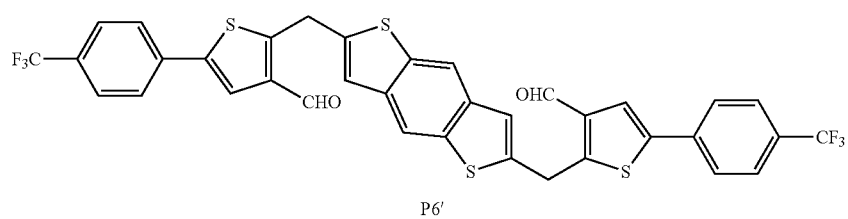

P6'

1.0 g (1.38 mmol) of P5' is dissolved in 120 ml of DCM and cooled down to a temperature of −10° C. Then 4.13 ml (4.13 mmol) of DIBAL-H is slowly added thereto. After 2 hours at −10° C., 1 N HCl (MeOH (3): H$_2$O (1)) is slowly added thereto. Then the temperature is slowly increased up to a room temperature. Then the organic layer is separated using water and DCM. It is purified by a column chromatography using chloroform to provide Compound P6' (yield: 50%).

(Synthesis of Compound P7')

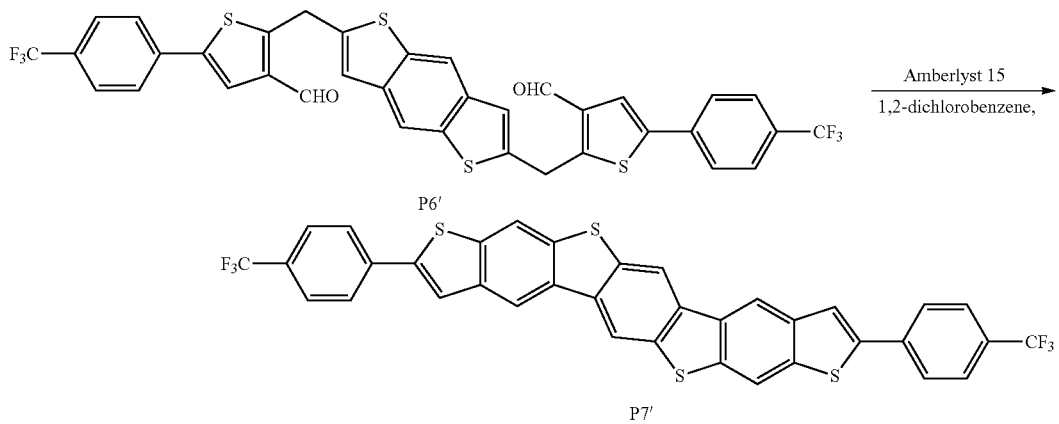

P6'

P7'

1.0 g of P6' and 1.0 g of Amberlyst 15, 20 ml of 1,2-dichorobenzene are placed in a vial and reacted in a microwave reactor at 120° C. for 10 hours. After the temperature is dropped to a room temperature, it is separated and purified by decanting the same using ethyl acetate to provide Compound P7' (yield: 50%).

Subsequently, the real structure of the final compound (Compound P7') obtained from Synthesis Example 2 is confirmed by MALDI-TOF mass analysis.

Figure 3:
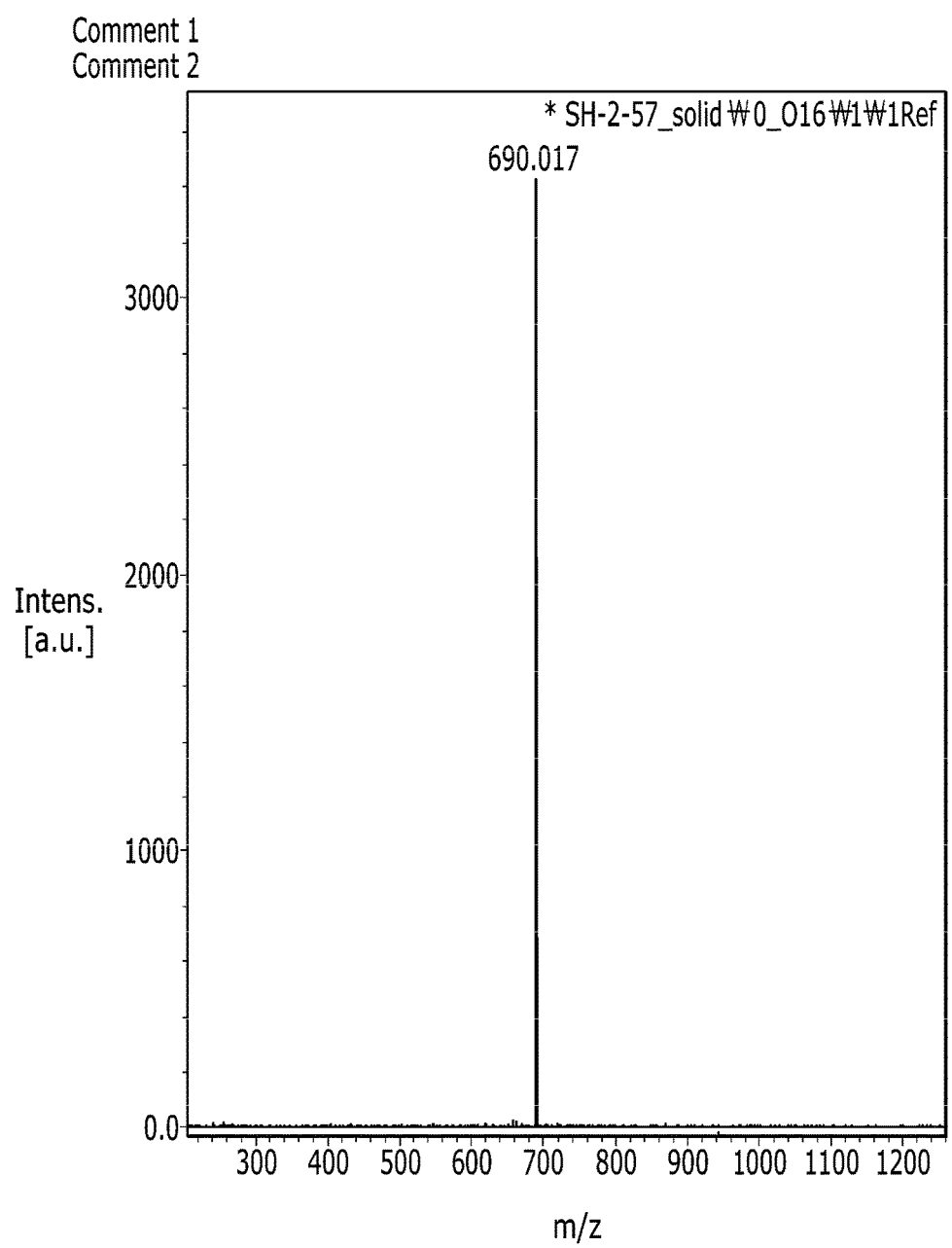
FIG. 3 shows an MALDI-TOF mass analysis data of the compound according to Synthesis Example 2.

FIG. 3 shows an MALDI-TOF mass analysis data of the final compound according to Synthesis Example 2 (m/z=690.017). Referring to FIG. 3, the compound of Synthesis Example is actually obtained.

Manufacture of Organic Thin Film Transistor

Example 1

First, a silicon wafer substrate covered with a cleaned SiO$_2$ in 3000 Å is exposed to O$_2$ plasma and then dipped in an octadecyltrichloro silane solution, which is diluted in hexane at a concentration of 10 mM, to change the surface to hydrophobicity. Subsequently, the organic compound obtained Synthesis Example 1 is deposited on a substrate in a thickness of 700 Å according to the vacuum vapor deposition while the temperature of substrate is changed from a room temperature to 200° C. Subsequently, source and drain electrodes are deposited by Au in a thickness of 1000 Å using a shadow mask to provide an organic thin film transistor.

Example 2

An organic thin film transistor is fabricated in accordance with the same procedure as in Example 1, except that the organic compound obtained from Synthesis Example 2 is used instead of the organic compound obtained from Synthesis Example 1.

Evaluation

A charge mobility of the organic thin film transistor according to Example 1 is calculated.

A graph with variations of $(I_{SD})^{1/2}$ and $V_{GS}$ is obtained from the saturation region current formula, and a charge mobility of the organic thin film transistor is obtained from the slope thereof:

$$I_{SD} = \frac{WC_0}{2L}\mu(V_{GS} - V_T)^2$$

$$\sqrt{I_{SD}} = \sqrt{\frac{\mu C_0 W}{2L}}(V_{GS} - V_T)$$

$$\text{slope} = \sqrt{\frac{\mu C_0 W}{2L}}$$

$$\mu_{FET} = (\text{slope})^2 \frac{2L}{C_0 W}$$

In Equation, $I_{SD}$ is a source-drain current; μ or $\mu_{FET}$ is a charge mobility; $C_0$ is a capacitance of gate insulating layer; W is a channel width; L is a channel length; $V_{GS}$ is a gate voltage; $V_T$ is a threshold voltage.

An off-state leakage current ($I_{off}$), which is a current flowing in off-state, is determined by the minimum current at the off-state in the current ratio. The current on-off ratio ($I_{on}/I_{off}$) is obtained by a ratio of the maximum current value at on-state to the minimum current value at off-state.

Figure 4:
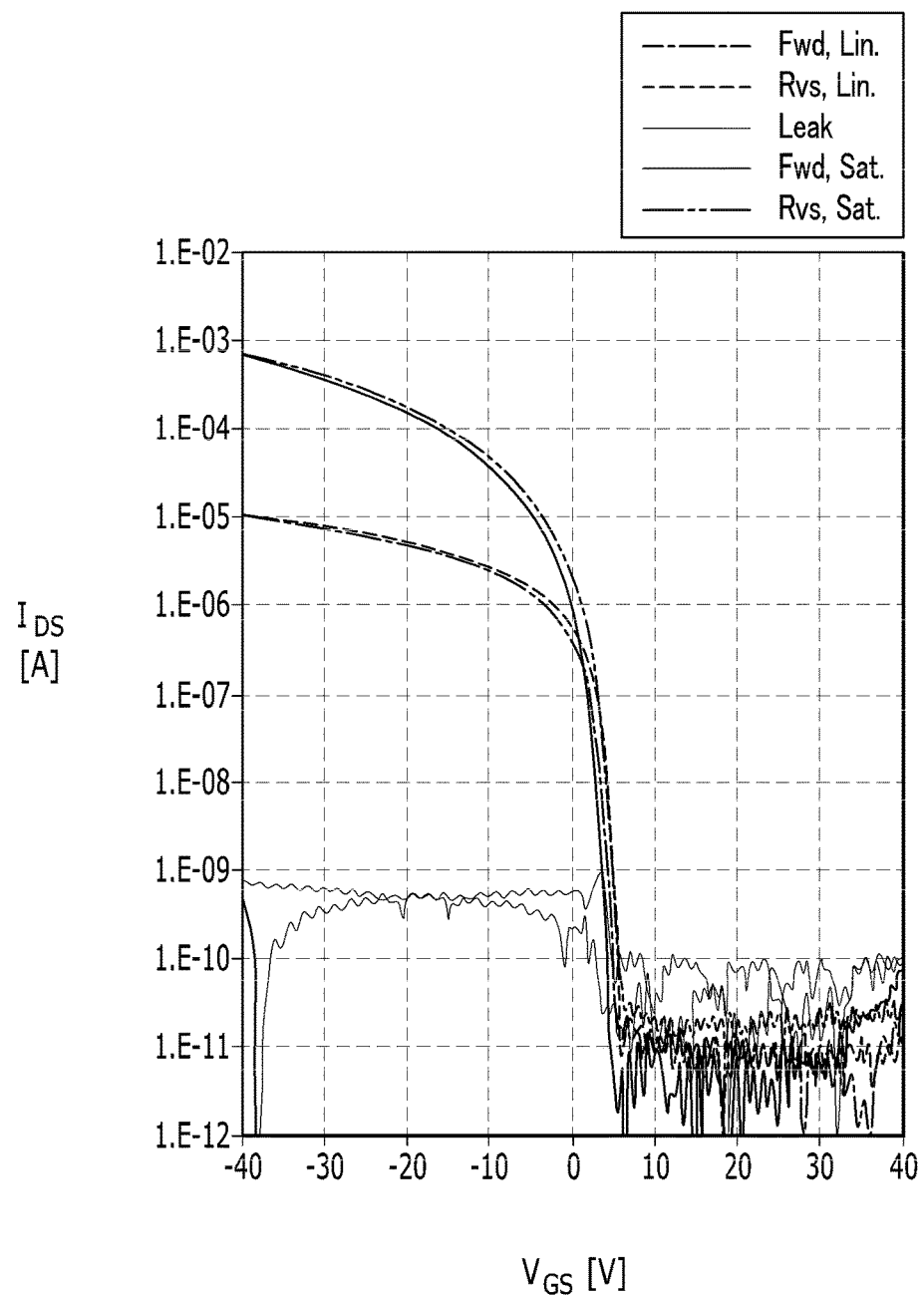
FIG. 4 is a graph showing charge mobility of the organic thin film transistor according to Example 1.
Figure 5:
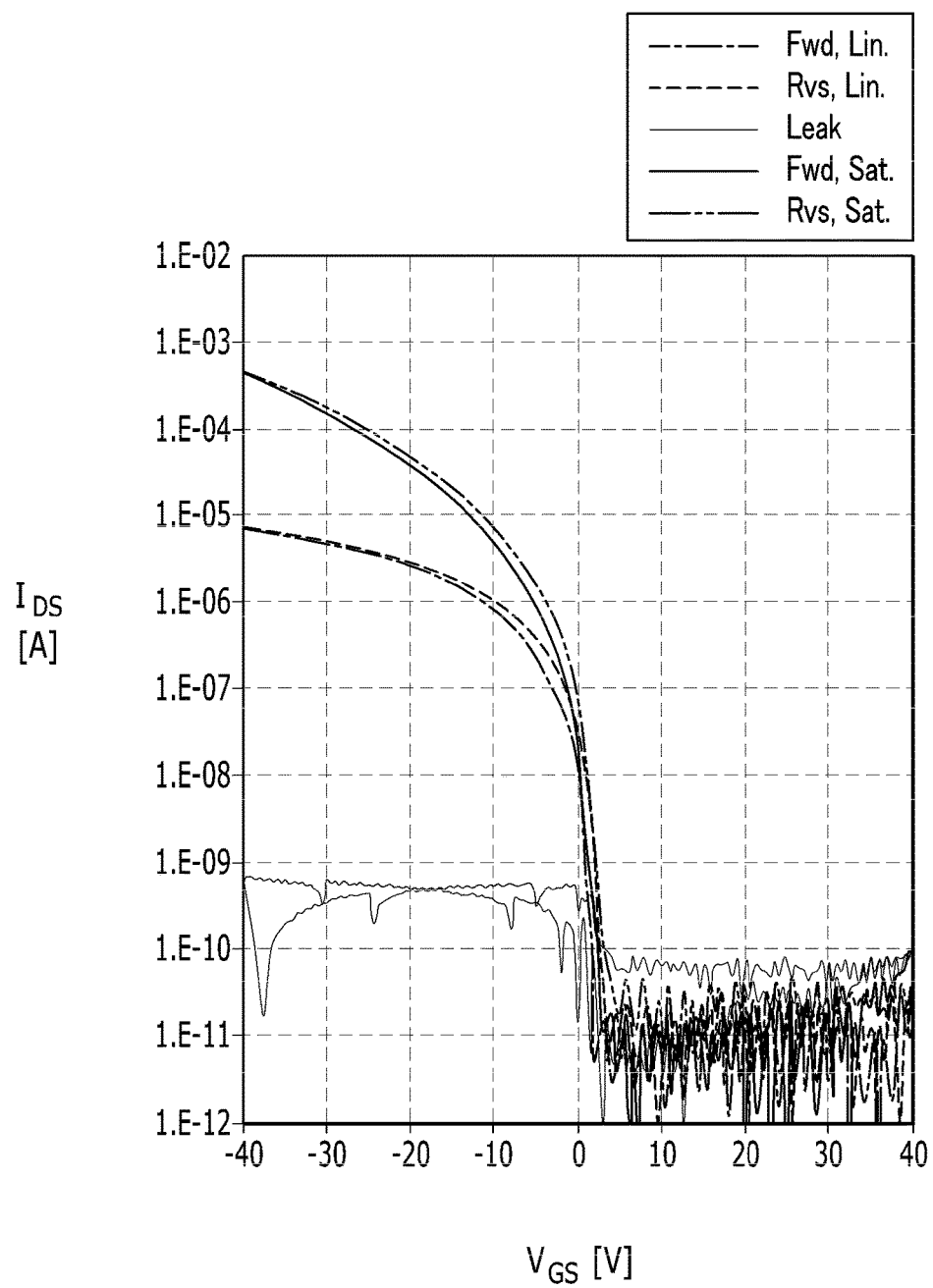
FIG. 5 is a graph showing charge mobility of the organic thin film transistor according to Example 2.

The results are shown in FIGS. 4 and 5 and Table 1.

FIG. 4 is a graph showing charge mobility of the organic thin film transistor according to Example 1 and FIG. 5 is a graph showing charge mobility of the organic thin film transistor according to Example 2.

TABLE 1

|  | Charge mobility (cm$^2$/Vs) | Maximum current value in on state (A) | Current on-off ratio ($I_{on}/I_{off}$) |
| --- | --- | --- | --- |
| Example 1 | 11.48 | 6.66 × 10$^{-4}$ | 3.00 × 10$^9$ |
| Example 2 | 14.63 | 3.81 × 10$^{-4}$ | 3.50 × 10$^9$ |

Referring to FIGS. 4 and 5 and Table 1, the thin film transistor according to Example 1 has charge mobility of greater than or equal to about 11 cm²/Vs and current on-off ratio of greater than or equal to about 10⁹, thereby having improved characteristics While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. An organic compound represented by Chemical Formula 1:

[Chemical Formula 1]

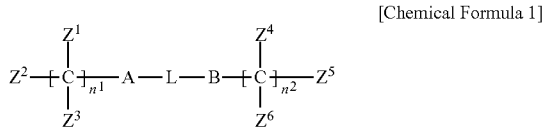

wherein in Chemical Formula 1,
each of A and B are independently one of a substituted or unsubstituted $C_6$ to $C_{30}$ arylene group, a divalent substituted or unsubstituted $C_2$ to $C_{30}$ heterocyclic group, and a combination thereof,
each of $Z^1$ to $Z^6$ are independently one of hydrogen, a $C_1$ to $C_{10}$ haloalkyl group, and a halogen, provided that at least one of $Z^1$ to $Z^6$ is one of a $C_1$ to $C_{10}$ haloalkyl group and a halogen,
each of $n^1$ and $n^2$ are independently an integer of 0 to 5, and
L is a condensed polycyclic group including 6 or more fused rings and a group represented by Chemical Formula 2,

[Chemical Formula 2]

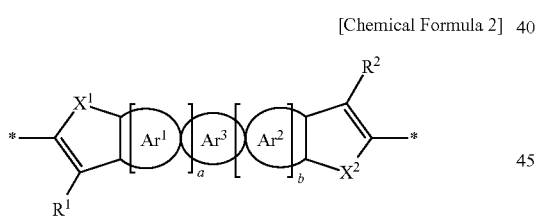

wherein, in Chemical Formula 2,
each of $Ar^1$ and $Ar^2$ are independently one of a substituted or unsubstituted five-membered ring and a substituted or unsubstituted six-membered ring,
$Ar^3$ is one of

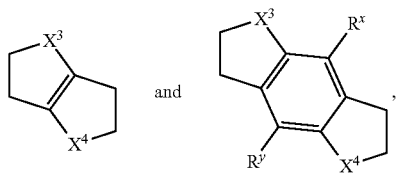

each of $X^1$ to $X^2$ are independently one of O, Se, Te, and $NR^a$,
each of $X^3$ to $X^4$ are independently one of O, S, Se, Te, and $NR^a$, each of $R^1$, $R^2$, $R^a$, $R^x$ and $R^y$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ lalkenyl group, a substituted or unsubstituted $C_2$ to $C_{30}$ alkynyl group, a hydroxy group, a halogen, and a combination thereof,
each of a and b are independently an integer ranging from 1 to 3, and
* is a linking point,
when in Chemical Formula 2, $Ar^3$ is

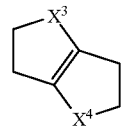

and a=b=1, the L is a group represented by Chemical Formula 3:

[Chemical Formula 3]

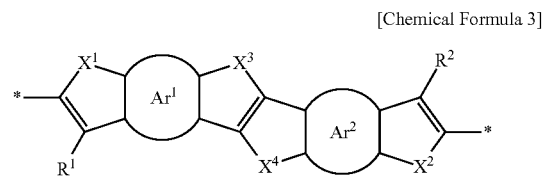

wherein, in Chemical Formula 3,
$Ar^1$, $Ar^2$, $X^1$ to $X^4$, $R^1$, $R^2$ and * are the same as defined in Chemical Formula 2.

2. The organic compound of claim 1, wherein each of the $Ar^1$ and $Ar^2$ groups are independently one of a substituted or unsubstituted benzene ring and a substituted or unsubstituted heterocyclic group.

3. The organic compound of claim 1, wherein each of the $Ar^1$ and $Ar^2$ groups are a substituted or unsubstituted benzene ring.

4. The organic compound of claim 3, wherein a and b satisfy one of a=b=1 and a=b=2.

5. The organic compound of claim 1, wherein the L is represented by one of the following compounds of Group 1:

[Group 1]

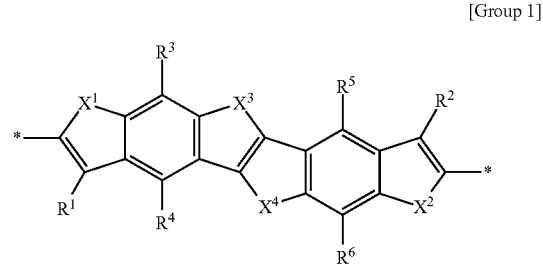

31
-continued

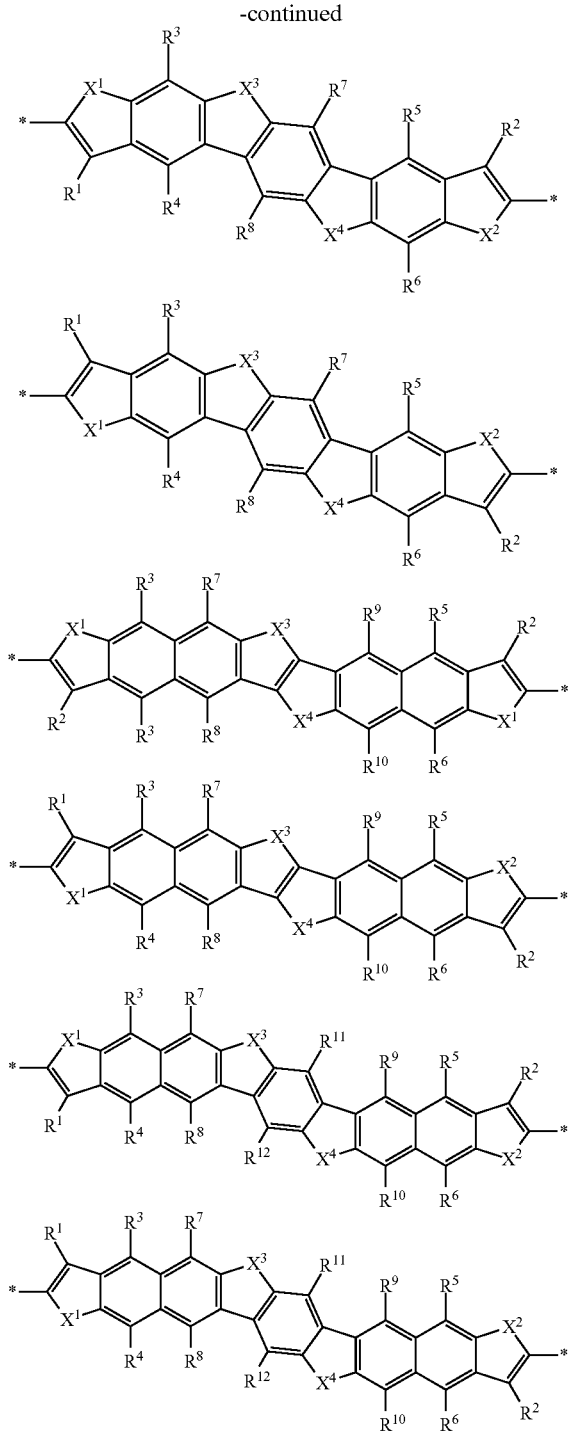

32 heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof, and

* is a linking point.

6. The organic compound of claim 1, wherein each of A and B is represented by one of the following compounds of Group 2:

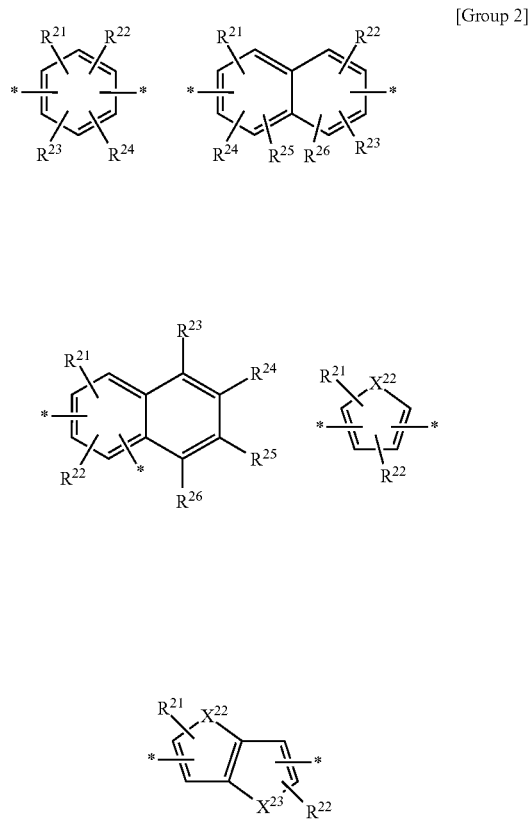

wherein, in Group 2, each of $X^{21}$ to $X^{23}$ are independently one of O, S, Se, Te, and $NR^a$, each of $R^{21}$ to $R^{26}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic , group, a substituted or unsubstituted $C_2$ to $C_{30}$ alkenyl group, a substituted or unsubstituted $C_2$ to $C_{30}$ alkynyl group, a hydroxy group, a halogen, and a combination thereof, and

* is a linking point.

wherein, in Group 1, each of $X^1$ to $X^2$ are independently one of O, Se, Te, and $NR^a$, each of $X^3$ to $X^4$ are independently one of O, S, Se, Te, and $NR^a$, each of $R^1$ to $R^{12}$ and $R^a$ are independently one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ 7. The organic compound of claim 1, wherein each of the $Z^1$ to $Z^6$ groups are independently a halogen.

8. The organic compound of claim 1, wherein the organic compound is represented by one of the following compounds of Group 3:

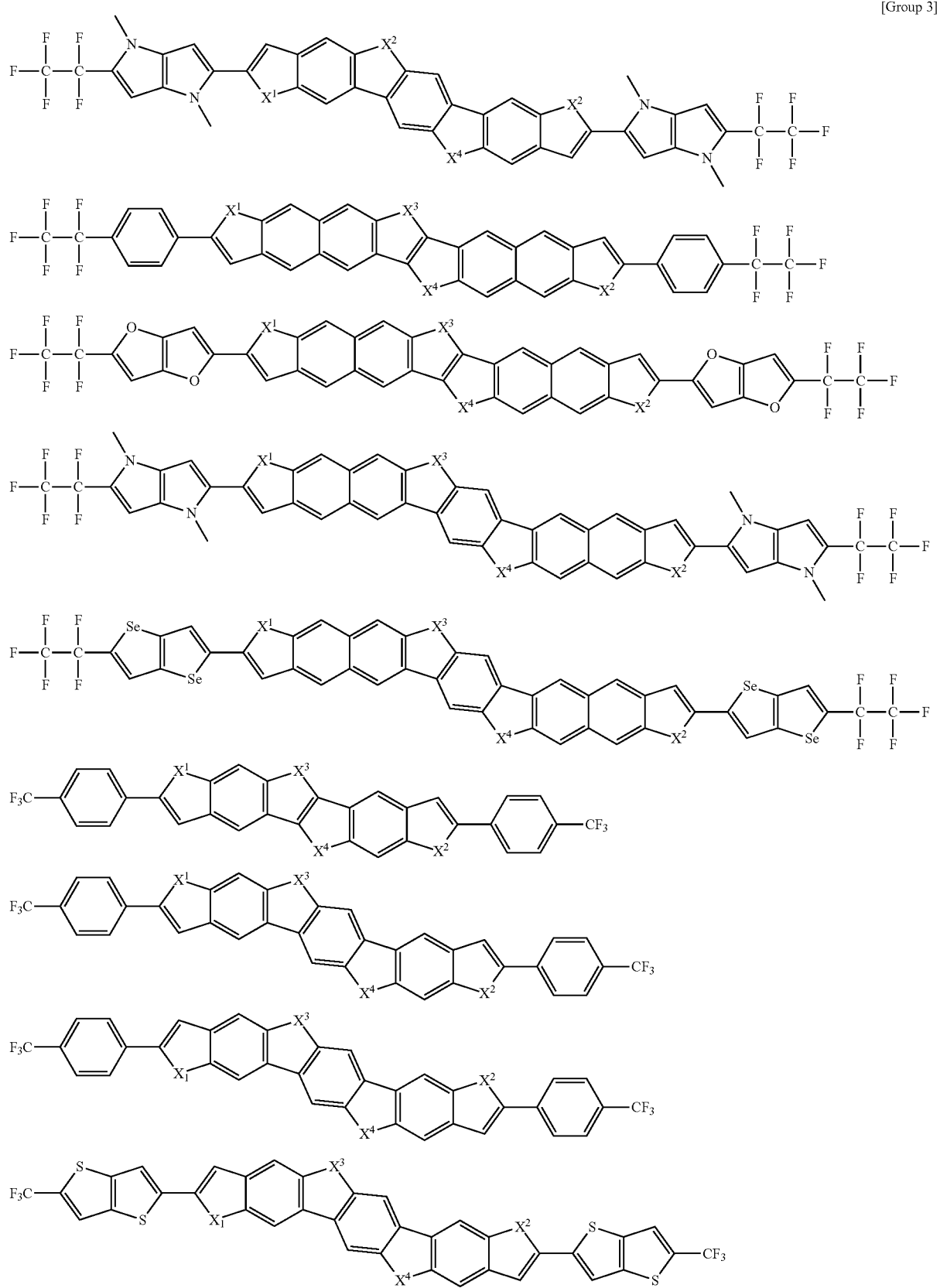
[Group 3]

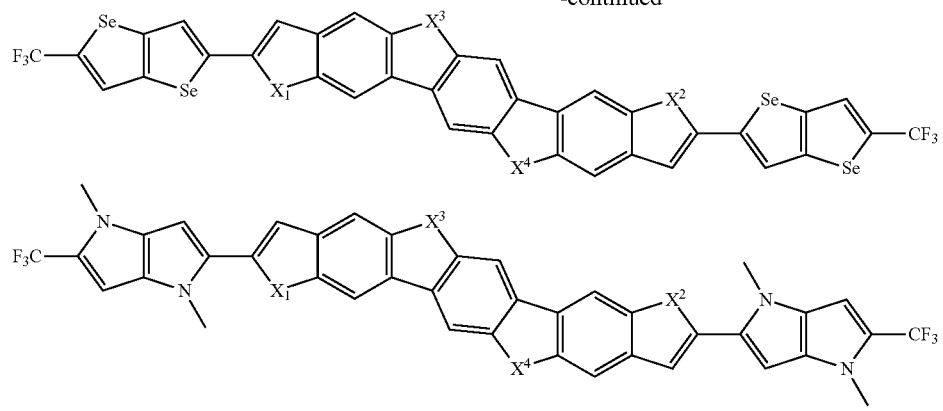

wherein, in Group 3, each of $X^1$ to $X^2$ are independently one of O, Se, Te, and $NR^a$, each of $X^3$ to $X^4$ are independently one of O, S, Se, Te, and $NR^a$, $R^a$ is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_7$ to $C_{30}$ arylalkyl group, a substituted or unsubstituted $C_1$ to $C_{30}$ heteroalkyl group, a substituted or unsubstituted $C_2$ to $C_{30}$ heterocycloalkyl group, a substituted or unsubstituted $C_2$ to $C_{30}$ heterocyclic group, a substituted or unsubstituted $C_2$ to $C_{30}$ alkenyl group, a substituted or unsubstituted $C_2$ to $C_{30}$ alkynyl group, a hydroxy group, a halogen, and a combination thereof.

9. An organic thin film comprising the organic compound of claim 1.

10. A thin film transistor comprising:
a gate electrode;
an organic semiconductor overlapping the gate electrode, the organic semiconductor including the organic compound of claim 1; and
a source electrode and a drain electrode electrically connected to the organic semiconductor.

11. An electronic device comprising the thin film transistor of claim 10.

12. The electronic device of claim 11, wherein the electronic device includes one of a solar cell, a liquid crystal display, an organic light emitting device, an electrophoretic device, an organic photoelectric device, and an organic sensor.

13. An electronic device comprising the organic thin film of claim 9.

* * * * *